United States Patent [19]

Nelson

[11] Patent Number: 5,714,759
[45] Date of Patent: Feb. 3, 1998

[54] OPTICAL SYSTEM WITH AN EXTENDED, IMAGED SOURCE

[75] Inventor: Shari Nelson, Westminster, Colo.

[73] Assignee: Ohmeda Inc., Liberty Corner, N.J.

[21] Appl. No.: 605,973

[22] Filed: Feb. 23, 1996

[51] Int. Cl.⁶ .................................................. G01N 21/35
[52] U.S. Cl. ............... 250/343; 250/339.02; 250/339.13
[58] Field of Search ................... 250/339.02, 339.06, 250/339.13, 343

[56] References Cited

U.S. PATENT DOCUMENTS

| | | | |
|---|---|---|---|
| 3,976,883 | 8/1976 | Krakow | 250/343 |
| 4,054,389 | 10/1977 | Owen | 356/189 |
| 4,157,470 | 6/1979 | Kotaka et al. | 250/345 |
| 4,158,772 | 6/1979 | Reedy | 250/338 |
| 4,180,734 | 12/1979 | Gedeon | 250/345 |
| 4,200,791 | 4/1980 | Burough | 250/343 |
| 4,467,203 | 8/1984 | Rappaport | 250/343 |
| 4,694,173 | 9/1987 | Wong | 250/343 |
| 4,888,484 | 12/1989 | Harvey | 250/343 |
| 4,899,053 | 2/1990 | Lai et al. | 250/343 |
| 4,914,719 | 4/1990 | Conlon et al. | 250/339 |
| 4,928,015 | 5/1990 | Butler et al. | 250/343 |
| 4,957,371 | 9/1990 | Pellicori et al. | 356/419 |
| 5,046,018 | 9/1991 | Flewelling et al. | 364/497 |
| 5,081,998 | 1/1992 | Yelderman et al. | 128/719 |
| 5,092,342 | 3/1992 | Hattendorff et al. | 128/719 |
| 5,166,755 | 11/1992 | Gat | 356/419 |
| 5,220,173 | 6/1993 | Kanstad | 250/493.1 |
| 5,260,574 | 11/1993 | Becker | 250/338.1 |
| 5,296,706 | 3/1994 | Graig et al. | 250/339 |
| 5,300,780 | 4/1994 | Denney et al. | 250/342 |
| 5,360,004 | 11/1994 | Purdy et al. | 128/633 |
| 5,379,764 | 1/1995 | Barnes et al. | 128/633 |
| 5,401,966 | 3/1995 | Gray et al. | 250/343 |
| 5,440,143 | 8/1995 | Carangelo et al. | 250/573 |
| 5,460,177 | 10/1995 | Purdy et al. | 128/633 |
| 5,461,477 | 10/1995 | Marinelli et al. | 356/352 |

OTHER PUBLICATIONS

Maris et al., "Nonlinear Multicomponent Analysis by Infrared Spectrophotometry", pp. 1694–1703, 1983, *Anal. Chem.*, vol. 55, No. 11, Sep.

*Primary Examiner*—Constantine Hannaher
*Attorney, Agent, or Firm*—William A. Schonemar; Roger M. Rathbun; Thomas R. Marsh

[57] ABSTRACT

The source (12) has a heater element (122) sandwiched between elongate emitter plates (124 and 126). In operation, the source (12) is operated at temperatures in excess of 900° C. and, preferably, at least about 1200° C. to provide radiation in the 7–10 micrometer wavelength range. In one embodiment, the source (12) is used in conjunction with an elongate detector array (14) in a gas analyzer (10) for analyzing respiratory and anesthetic gases. Spherical mirrors (36a, 36b) and flat mirrors (38a, 38b) are employed to image the source (12) on the detector array (14). A linear variable filter (26) allows for analysis of the radiation at multiple wavelengths using detector array (14).

20 Claims, 5 Drawing Sheets

OPTICAL SYSTEM WITH AN EXTENDED, IMAGED SOURCE

FIELD OF THE INVENTION

The present invention relates generally to radiation sources and associated optical systems, i.e., systems involving the transmission of infrared (IR), visible or ultraviolet radiation. In particular, the present invention relates to an optical system including an extended IR source that is imaged on an extended detector. The system facilitates efficient multiple analyses relative to a longitudinal dimension of the imaging beam and is particularly apt for use in a polychromatic gas analyzer.

BACKGROUND OF THE INVENTION

Optical systems are employed in a variety of contexts where it is desired to perform multiple analyses of a subject. The case of gas analyzers is illustrative. Gas analyzers are used in various medical and industrial applications to monitor the presence and concentration of selected components in a gaseous sample. In the medical context, gas analyzers are used to monitor the delivery of anesthesia by analyzing a respiratory stream with respect to selected respiratory and anesthetic components. In this regard, it may be desired to monitor respiratory gases such as oxygen and carbon dioxide, and one or more analgesic/anesthetic agents such as nitrous oxide, halothane and isoflurane. Monitoring anesthesia may therefore involve analyzing the respiratory stream with respect to one or multiple components.

Spectral gas analyzers provide an indication of the presence and concentration of selected components in a gas sample based on the detected spectral composition of radiation transmitted through the gas sample. The gaseous components of interest can be characterized with regard to specific radiation absorption properties. For example, a particular gaseous component may be characterized by an absorption band at a particular wavelength or wavelength range. By comparing the intensity of transmitted and received radiation of a selected wavelength for a particular gas sample, information regarding the absorption characteristics and composition of the sample can be obtained.

In order to analyze multiple components in a gas sample, radiation transmitted through the gas sample can be separately analyzed at multiple wavelengths. Some conventional gas analyzers conduct such multiple wavelength analyses by sequentially positioning optical band pass filters with different wavelength transmissivity characteristics in the analyzer beam path. Other conventional gas analyzers employ multiple, spaced detectors with associated filters, all in the area of a broad beam.

SUMMARY OF THE INVENTION

The present invention is directed to a source and an optical system for facilitating multiple analyses with respect to a beam cross-section. It has been recognized that systems which sequentially position filters in a beam path are unduly complex and slow. Systems that position multiple spaced detectors and associated filters in a broad beam path tend to inefficiently use source energy as significant radiation may go undetected. A higher energy source may therefore be required which can also result in undesired heat, particularly where high temperature IR sources are involved. The present invention facilitates multiple analyses relative to a beam cross-section while making efficient use of source energy.

According to one aspect of the present invention, a novel IR source is provided. The IR source comprises an electrical resistance heater element in thermal contact with an elongate emitter plate. Preferably, the emitter plate has a substantially planar emitter surface and, more preferably, has two, oppositely directed substantially planar emitter surfaces for illuminating two optical paths. In one embodiment the surface has a width of at least about 3 mm and a length of at least about 12 mm. The emitter may be constructed from black silicon nitride. The heater element is adapted for interconnection to an external power source which may provide power at 100 V rms. The IR source is preferably operated at a temperature greater than 900° C. and emits blackbody radiation including radiation in the 7 to 10 micrometer wavelength region. More preferably, the IR source is operated at a temperature of at least about 1200° C. Operation in the preferred temperature ranges has been found to facilitate highly accurate analysis, with an improved signal-to-noise ratio, in the system described in detail below.

According to another aspect of the invention, an optical system with an imaged IR source is provided. The system includes a source of IR radiation, a detector having a detector surface and imaging optics for imaging the source on the detector surface, i.e., for collecting radiation from the source so as to define an image of the source on the detector surface. The source, which may comprise a coil or emitter plate, is preferably elongate in form. In this manner, multiple analyses can be conducted relative to a longitudinal axis of the radiation beam. For example, multiple filters or a variable filter can be employed to allow polychromatic analysis across the length of the beam. In addition, the source preferably provides a relatively uniform radiation emission distribution across a longitudinal axis of the source. In this regard, a substantially planar emitter may be preferred over a coil emitter for applications where uniform distribution is important as hot spots can occur at coil winding edges. The detector surface, which can include multiple detector elements, is preferably dimensioned to substantially match the beam cross-section for enhanced efficiency.

According to a further aspect of the present invention, an imaged source optical system is employed in a gas analyzer. The gas analyzer includes: a source of radiation, preferably infrared; a detector having a detector surface; imaging optics for imaging the source on the detector surface; and a gas sample chamber disposed on an optical path between the source and detector. The sample chamber is preferably located between the imaging optics and the detector. For enhanced analysis of respiratory and anesthetic gases, the source preferably has a primary output band including the 7 to 10 micrometer wavelength range. Moreover, the source is preferably operated at a temperature greater than 900° C. and, more preferably, at least about 1200° C.

In one embodiment, a gas analyzer constructed in accordance with the present invention includes an IR source formed from a heater element sandwiched between two elongate, black silicon nitride plates. The source is operated at about 1200° C. by a 100V rms power source to provide radiation encompassing the 7 to 10 micrometer wavelength range. The radiation is collected by a spherical mirror to form a converging beam which is directed at a detector surface via a gas sample chamber, containing respiratory and anesthetic gas to be analyzed, and a linear variable filter. The optics and detector are arranged so that the source is imaged on the detector surface. The detector is comprised of a linear array of detector elements to separately detect radiation in bands across the wavelength range as selectively passed by the linear variable filter. In this manner, an accurate polychromatic analysis of the beam can be used to simultaneously yield information regarding multiple gaseous components.

BRIEF DESCRIPTION OF THE DRAWINGS

For a more complete understanding of the present invention and further advantages thereof, reference is now made to the following detailed description, taken in conjunction with the drawings, in which.

DETAILED DESCRIPTION OF THE PREFERRED EMBODIMENT

The source and optical system of the present invention are useful in a variety of contexts including spectral gas analysis for analyzing a gas sample with respect to the presence and/or concentration of one or more gaseous components. In this context, the analyzer configuration, selected wavelengths and various other factors may be varied depending on space requirements, the transmissivity/absorption characteristics of the gaseous components(s) of interest and the like. In the following description, the invention is set forth with respect to a specific embodiment for analyzing respiratory and anesthetic gases.

Figure 1:
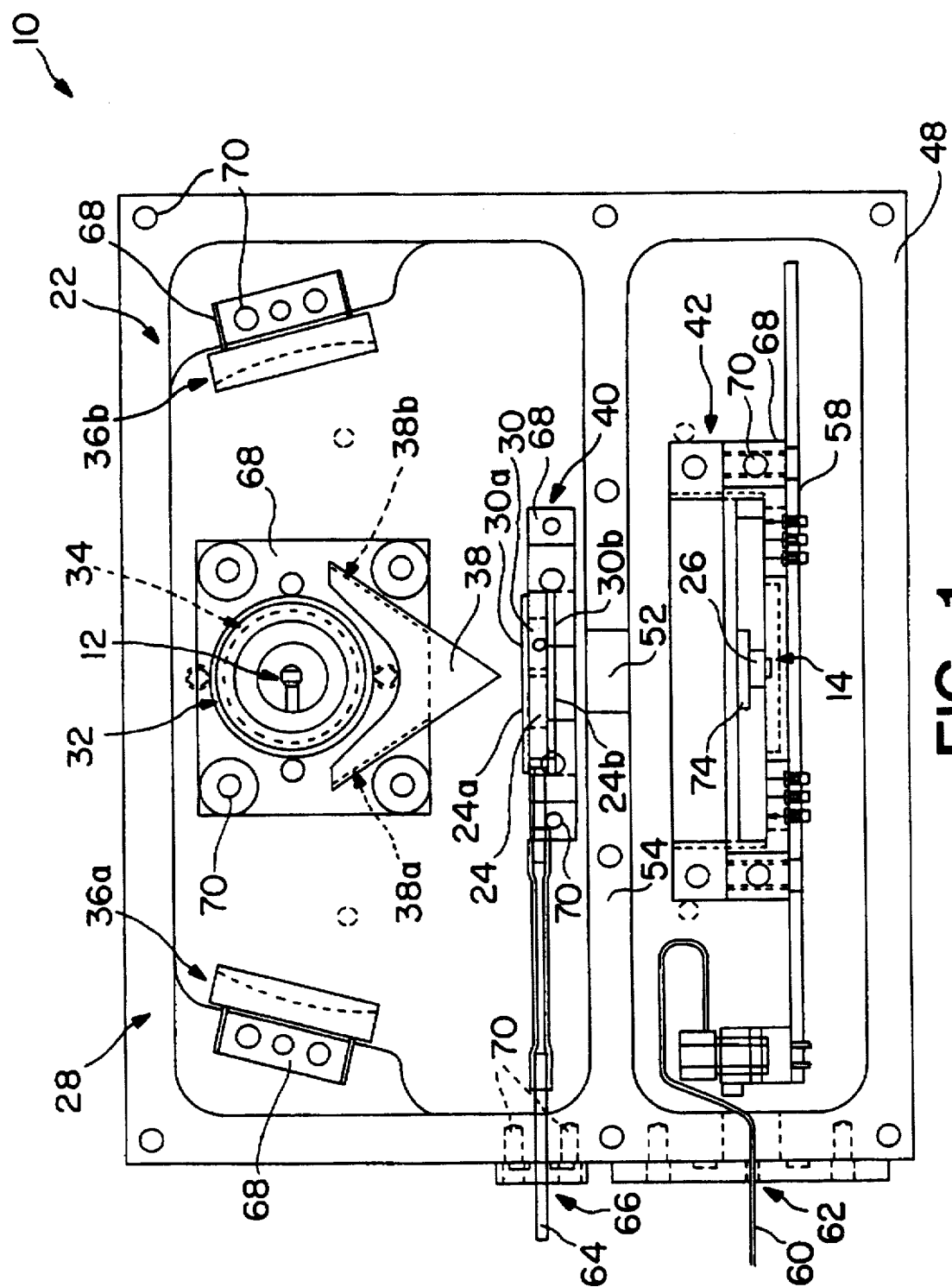
FIG. 1 is a top view of a gas analyzer according to the present invention.
Figure 3:
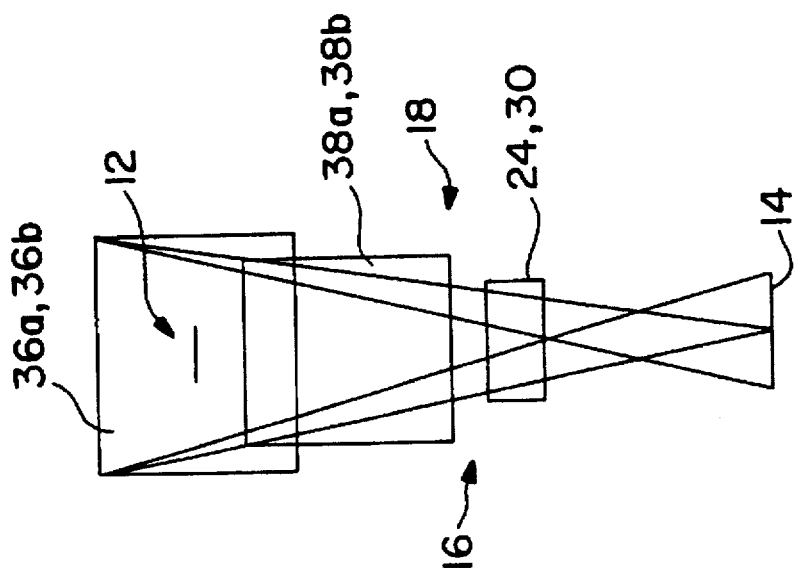
FIG. 3 is a side view illustrating optical pathways of the gas analyzer of FIG. 1.
Figure 2:
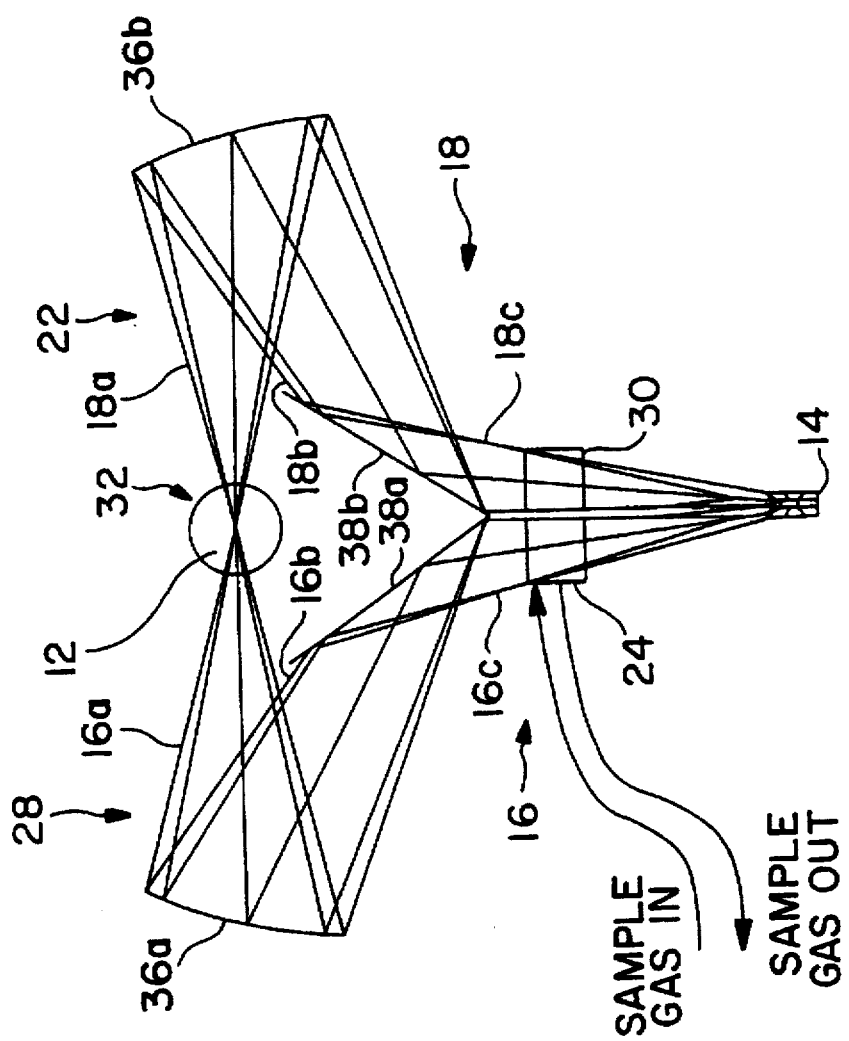
FIG. 2 is a top schematic view illustrating optical pathways of the gas analyzer of FIG. 1.
Figure 4A:
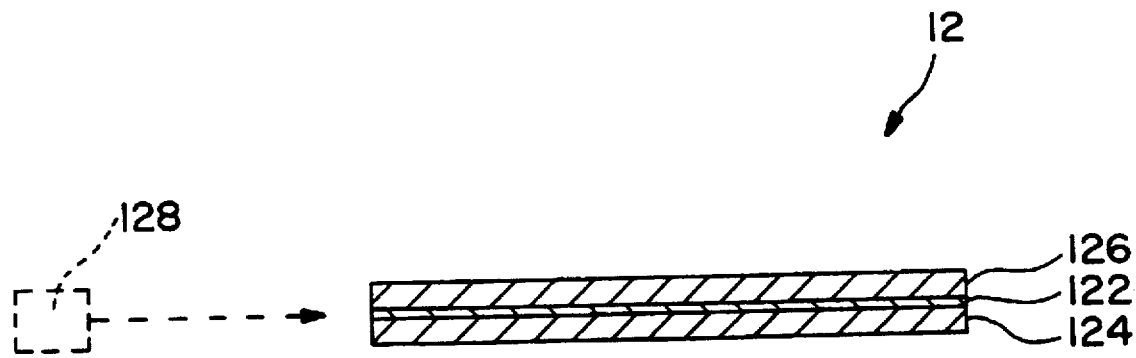
FIGS. 4a and 4b are side and bottom views, respectively, of the source of the gas analyzer of FIG. 1.
Figure 4B:
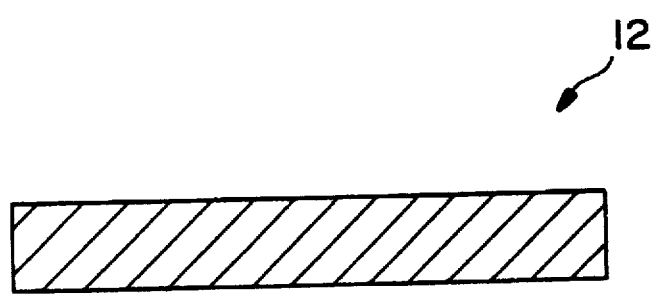
Figure 5:
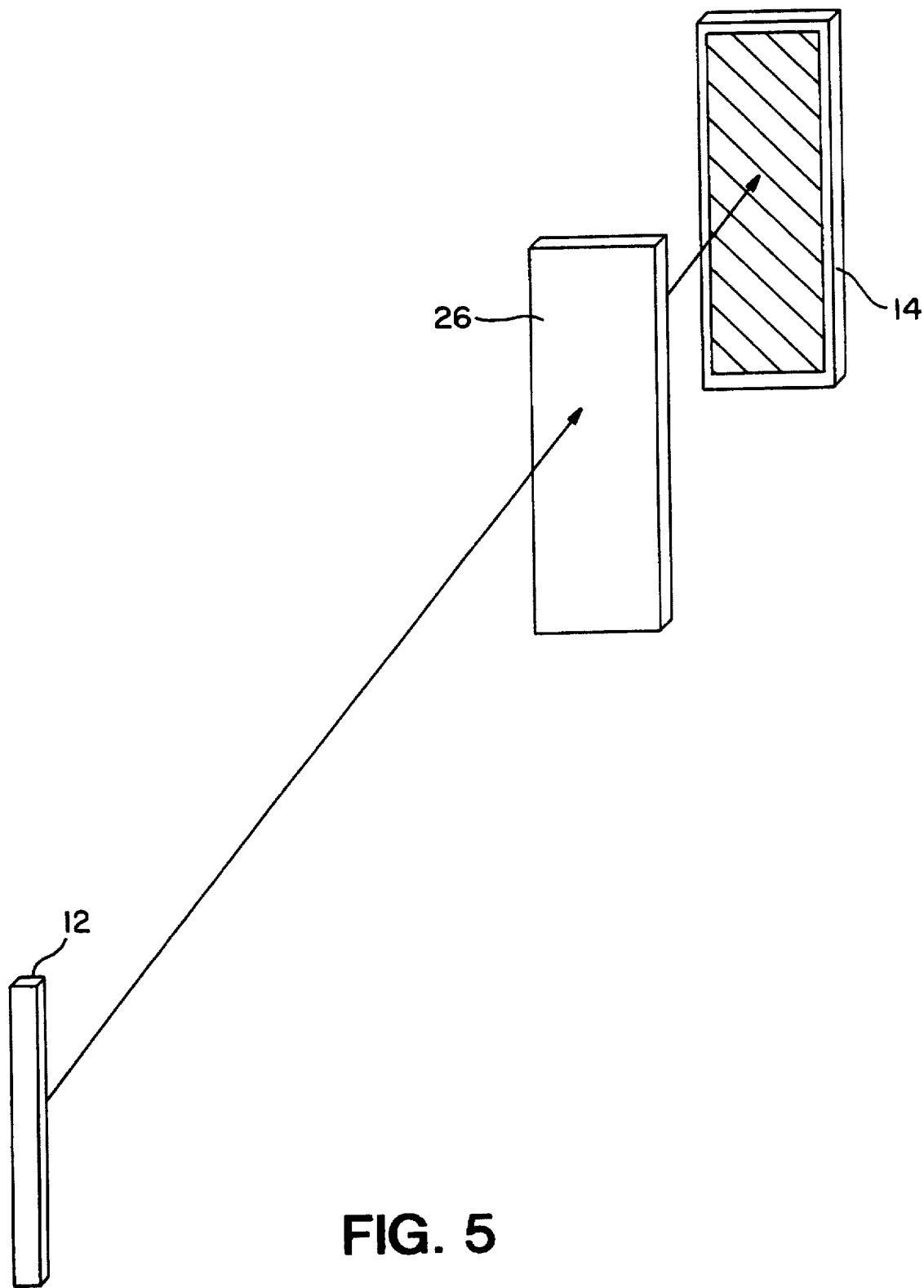
FIG. 5 is a schematic front perspective view showing radiation imaged on the filter/detector assembly of the gas analyzer of FIG. 1.
Figure 6:
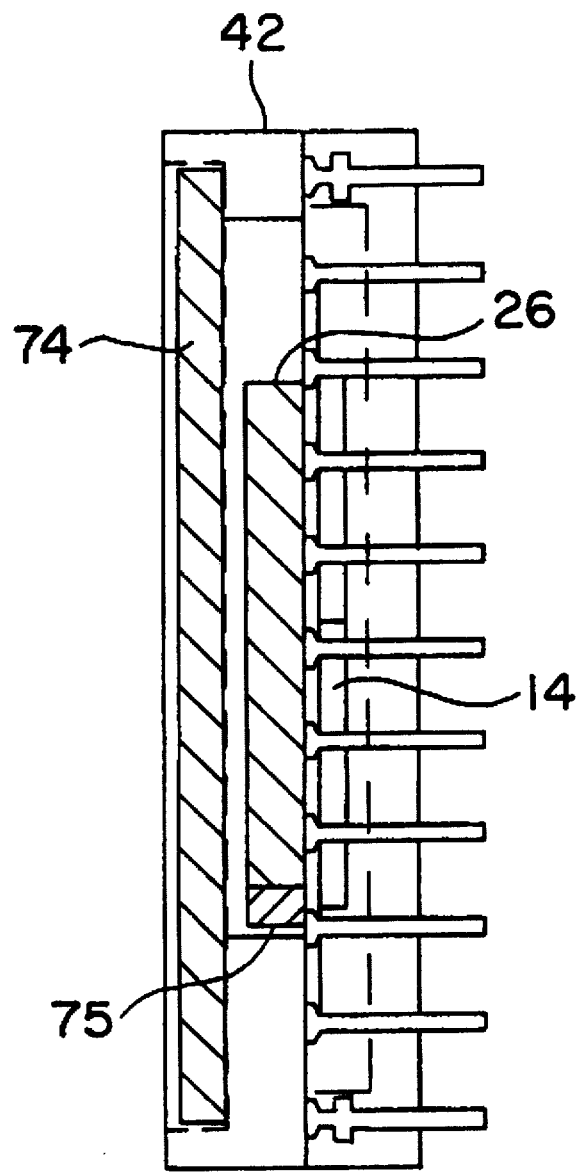
FIG. 6 is a side view of the filter/detector assembly of the gas analyzer of FIG. 1.

Referring to FIGS. 1–6, a folded optical path implementation of the gas analyzer 10 is illustrated. FIG. 1 illustrates various system components in detail and FIGS. 2 and 3 show optical schematics for the analyzer 10. FIGS. 4a and 4b show side and bottom views respectively of the novel source 12 employed in the gas analyzer 10. FIGS. 5–6 show details of the filter/detector assembly 42 of the gas analyzer 10.

Generally, the gas analyzer 10 includes an upstanding IR radiation source 12 positioned within a concentric, rotatable, cylindrical beam chopper 32 having at least one pass-through window or slit 34 in a portion of the side wall thereof, two spherical mirrors 36a, 36b, a flat mirror block 38 having flat mirrors 38a, 38b, a dual gas chamber member 40 having a sample gas chamber 24 and a reference gas chamber 30, and a filter/detector assembly 42 having polychromatic filter 26 and detector array 14, all mounted within frame 48.

As shown in the optical path schematics in FIGS. 2–3, the infrared source 12 emits radiation which, by virtue of the rotation of the chopper 32, results in the alternate impingement of beams 16a and 18a on spherical mirrors 36a and 36b, respectively. In turn, convergent beams 16b and 18b respectively reflect off spherical mirrors 36a and 36b and impinge on flat mirror elements 38a and 38b. The reflected infrared beams 16c and 18c then pass through sample gas chamber 24 and reference gas chamber 30, respectively, before impinging on detector array 14. The optics are designed so that the source 12 is imaged on the detector array 14 as shown in FIG. 5, where the shaded area on detector array 14 represents the imaged source radiation. That is, the radiation is focused by the optics to define an image of the source 12 on the detector array 14. As shown, the detector array is thereby substantially completely illuminated and source energy losses are minimized. In this regard, in the illustrated embodiment, the source 12, filter 26 and array 14 are arranged in an aligned upstanding orientation.

The illustrated source 12 irradiates optical paths 16 and 18 with radiation encompassing a characteristic absorption band of at least one respiratory/anesthetic component of interest. Although various wavelengths or spectra can be employed including IR, visible and ultraviolet wavelength ranges, the illustrated source 12 is a polychromatic (black body) IR source transmitting radiation encompassing, for example, the 7–10 micrometer wavelength range, which includes strong absorption bands of several respiratory/anesthetic components.

The source 12, as shown in FIGS. 4a and 4b, is constructed in the form of an elongate, substantially homogeneous strip. As described below, the detector of the illustrated system is comprised of an elongate, columnar array of detector elements, e.g., a 1 by N array. The detector array is employed in conjunction with a polychromatic filter so that the array elements provide intensity detection for multiple wavelengths or wavelength bands across a desired spectral range. The elongate, homogeneous source 12, in combination with the illustrated imaging optics, allows complete, substantially even and intense illumination of the detector array for enhanced polychromatic analysis.

The source 12 includes a heater element 122 sandwiched between emitter plates 124 and 126. The heater element 122, which can be any suitable electrical resistance element, is preferably screened onto one of the plates 124 or 126 which serves as a substrate, although separate resistance wires may be employed. The illustrated plates 124 and 126 are constructed from black silicon nitride and are about 3 to 3.5 mm wide with a length of approximately 12 min. The leads to the illustrated heating element are connected to a power source directly through the substrate silicon nitride plate 124 or 126. In order to provide the desired illumination, the source is preferably operated at a temperature greater than 900° C. The illustrated source 12 is powered by a 100V rms power source 128 and reaches a temperature of approximately 1200° C. Operation in the preferred ranges has been found to provide an improved signal to noise ratio and improved overall performance in the context of the illustrated high frequency chopped optical path gas analyzer 10.

Referring to FIG. 1, the IR source 12 is mounted within cylindrical beam chopper 32. The rotatable beam chopper 32 alternately transmits radiation from source 12 via the sample 16 and reference 18 optical paths (FIG. 2) and also contains, to an extent, heat generated by the source 12. The illustrated chopper 32 includes a single slit 34 in its cylindrical sidewall. Additionally, as shown, the source 12 and the spherical mirrors 36a and 36b are geometrically arranged in a substantially linear relationship. That is, the mirrors 36a and 36b are located about 180° apart relative to the source 12. It will be appreciated that the illustrated arrangement allows for convenient variable duty cycle usage by appropriate chopper operation and detector cycling. For example, the chopper 32 of the illustrated embodiment can be operated at 20 revolutions per second. In this regard, the detector array 14 can be read out at intervals coordinated with the rotation rate of the chopper 32.

The geometric arrangement of spherical mirrors 36a, 36b, flat mirrors 38a, 38b, and chambers 24, 30, defines the optical paths 16, 18 such that the beam incidence angles on the polychromatic filter 26 are nearly normal. In order to enhance operation of the filter/detector 42, it is preferred that incidence angles be much less than 30°–35° from normal (e.g., the angle that would be obtained if radiation was reflected directly from the spherical mirrors 36a, 36b to the detector 14 without intervening flat mirrors 38a, 38b). More preferably, the incidence angles are less than about 15° from normal to reduce spectral smearing. In the illustrated embodiment, as shown most clearly in FIGS. 2–3, the limit incidence angles are less than about 15° from normal, e.g., about 10° for centrally located pixels of the detector array and 14° for outer pixels, all within filter specifications.

Referring to FIGS. 1 and 6, after irradiating chambers 24 and 30, converging beams 16c, 18c pass through transparent window 52 in thermal isolation wall 54 of structural frame 48 and filter 26 and impinge upon detector array 14. A band pass filter 74 may be positioned in front of the polychromatic filter 26 to selectively pass radiation in the wavelength range of interest and reduce interference. In addition, a separate filter 75 (shown in FIG. 6 but not in FIG. 1), such as a sapphire $CO_2$ filter, may be positioned in adjacent, stacked relation to the polychromatic filter 26 for use in analyzing a specific component. Filter 26, as discussed above, is a polychromatic filter including multiple sections that are selective for multiple wavelengths or wavelength ranges of interest. In this regard, the filter 26 can be formed as an array of bandpass filters arranged side-by-side in the beampaths. More preferably, the filter 26 comprises a linear variable filter that provides substantially linearly varying wavelength response characteristics across a beamwidth. Such a filter can be formed by depositing a stack of alternating high and low index of refraction materials on a filter substrate, where the stack layers are tapered in a controlled manner to yield the desired wavelength response variation. The illustrated filter provides substantially linearly varying wavelength response across, for example, the approximately 7–10 micrometer wavelength range.

The illustrated detector array 14 includes a single column of pyroelectric or heat sensitive elements and is supported by a detector board 58 carrying the circuitry for reading out the detector array 14, e.g., serial clocking circuits. The read out clocking of the detector array 14 can be readily coordinated with the chopper rotation rate to provide alternate sample and reference readout values. In this regard, the 180° spacing of the spherical mirrors 36a and 36b relative to the source 12 allows for convenient interval clocking. Such coordination may be accomplished, for example, by indexing the read out clocking to pulses from an encoder or motor associated with the chopper 32.

It will be appreciated that specific elements of the array 14 are associated with specific wavelength bands of filter 26. A polychromatic analysis of an incident beam can therefore be obtained by correlating the output from a particular element, or group thereof, and the associated wavelength band. This information can be used by a processor to determine gaseous composition information pertaining to multiple gaseous components.

FIG. 1 also shows: electrical wires 60 and associated housing pass-through 62 for interconnecting the detector array 14 to a processor; gas inlet tubes 64 and an associated housing pass-through 66 for supplying a sample gas to the chamber 24; and various mounts 68 and mounting holes 70 for mounting the various system components within frame 48 or interconnection to related housings. Although not shown, it will be appreciated that sample chamber 24 communicates with a supply of respiratory/anesthetic gases by way of appropriate fluid flow control devices.

The illustrated gas analyzer thus provides a polychromatic analysis of multiple gaseous components in a respiratory/anesthetic sample by employing a single elongate IR source, single detector array and polychromatic filter unit interrelated by folded optical paths. The collection optics serve to image the source on the detector array for enhanced efficiency and can be disposed upstream from the gas chamber so that beams exiting the gas chambers are directly received by the filter/detector. The chopper provides convenient duty cycle selection for alternate illumination of the symmetrical reference and sample paths.

While various embodiments of the present invention have been described in detail, it is apparent that further modifications and adaptations of the invention will occur to those skilled in the art. However, it is to be expressly understood that such modifications and adaptations are within the spirit and scope of the present invention.

I claim:

1. A respiratory and anesthetic gas analyzer, comprising:
   an elongated source of infrared radiation for transmitting polychromatic infrared radiation that encompasses a 7 to 10 micrometer wavelength range, said elongated source having a first longitudinal axis;
   a detector array for substantially simultaneously detecting said polychromatic radiation across the wavelength range and including a detector array surface, the detector array having a second longitudinal axis;
   optical imaging means for defining an optical path for imaging said source onto and across said detector array surface, wherein infrared radiation from said source impinging on said detector array surface defines an image of said elongated source, and wherein the first longitudinal axis of the source, when imaged on the detector array surface, is aligned with the second longitudinal axis of said detector array;
   a gas sample chamber, including a sample gas to be analyzed, disposed on the optical path.

2. The apparatus of claim 1, further comprising a linear variable filter disposed between the source and the detector array surface and having a center axis, the center axis being aligned with the first and second longitudinal axes when the source is imaged on the detector array surface.

3. The gas analyzer of claim 2, wherein the source, filter, and detector array are arranged in an aligned upstanding orientation.

4. The apparatus of claim 1, wherein said source comprises a substantially planar radiation emitter surface.

5. The apparatus of claim 1, wherein said source comprises two, oppositely facing substantially planar radiation emitter surfaces.

6. The apparatus of claim 1, wherein said source has a primary radiation band including the 7 to 10 micrometer wavelength range.

7. The apparatus of claim 1, wherein said source operates at a temperature greater than 900° C.

8. The apparatus of claim 1, wherein said source operates at a temperature of at least about 1200° C.

9. The apparatus of claim 1, wherein said detector surface is dimensioned to substantially match said image of said source.

10. A gas respiratory and anesthetic analyzer, comprising:
    an elongated radiation source for emitting polychromatic radiation including the 7 to 10 micrometer wavelength range, the elongated radiation source having a first longitudinal axis;
    a detector array for substantially simultaneously detecting the polychromatic radiation across the wavelength range and including a detector array surface, the detector array being aligned relative to a second axis;

optical imaging means for defining first and second optical paths from said source to said detector array, wherein radiation sequentially passing along the first and second optical paths and impinging on said detector surface defines an image of said source across said detector array surface such that the first longitudinal axis of the source, when imaged on the detector array surface, is aligned with the second axis; and a gas sample chamber, including a sample gas to be analyzed, disposed on at least one of said first and second optical paths.

11. The gas analyzer of claim 10, further comprising a polychromatic filter disposed along at least one of the first and second optical path, the filter having a third longitudinal axis that is aligned with the first and second longitudinal axes.

12. The gas analyzer of claim 10, wherein said source comprises a substantially planar radiation emitter surface.

13. The gas analyzer of claim 10, wherein said source operates at a temperature greater than 900° C.

14. The gas analyzer of claim 10, wherein said source operates at a temperature of at least about 1200° C.

15. The gas analyzer of claim 10, wherein said detector surface is dimensioned to substantially match said image of said source.

16. The gas analyzer of claim 10, wherein said gas sample chamber is disposed between said optical imaging means and said detector.

17. The gas analyzer of claim 10, wherein a first radiation portion is passed along the first optical path and a second radiation portion is passed along the second optical path and the first and second radiation portions each have a common predetermined band of wavelengths.

18. A respiratory and anesthetic gas analyzer, comprising:

an elongate infrared radiation source, having a first longitudinal axis, for transmitting polychromatic infrared radiation including a wavelength band ranging from about 7 to about 10 micrometers;

a radiation detector array for substantially simultaneously receiving said infrared radiation across the wavelength range from said radiation source, said array having a plurality of radiation sensitive elements that are aligned relative to a second axis;

a polychromatic filter for filtering said infrared radiation from said radiation source, said filter including a plurality of filter portions having differing wavelength dependent radiation transmission characteristics, said filter being oriented such that each of said plurality of filter portions is optically associated with one of said plurality of radiation sensitive elements, the plurality of filter portions being aligned relative to a third axis;

optical means for defining an optical path for imaging said infrared source onto and across said radiation detector array and said polychromatic filter such that said infrared source is imaged simultaneously on the plurality of radiation sensitive elements and the plurality of filter portions, wherein said wavelength band of infrared radiation from said source impinging on said detector array and said plurality of filter portions defines a polychromatic image of said source such that said first longitudinal axis of said source, when imaged on said detector array, is aligned with said second axis of said array and said third axis of said plurality of filter portions; and a gas sample chamber, wherein the detector array, polychromatic filter, and gas sample chamber are disposed on the optical path.

19. A method for analyzing respiratory and anesthetic gas comprising the steps of:

placing a sample gas in a sample chamber;

emitting polychromatic radiation encompassing a wavelength range of approximately 7 to 10 micrometers from an elongated source having a first longitudinal axis;

directing the radiation through the sample chamber;

imaging the polychromatic radiation source through the sample chamber and onto and across a radiation detector array having a plurality of radiation sensitive elements aligned to a second axis, wherein radiation across said wavelength range is substantially simultaneously detected;

aligning said first longitudinal axis of said source with said second axis of said radiation detector array;

filtering said radiation with a polychromatic filter having a plurality of filter portions having differing wavelength dependent transmission characteristics;

orienting said filter so that each of said plurality of filter portions is optically associated with one of said plurality of radiation sensitive elements.

20. The method for analyzing gas of claim 19 wherein the step of emitting radiation further comprises:

positioning a heating element and a substantially planar emitter plate in thermal contact to define said source;

connecting the heater element to a power source; and operating the power source to heat the emitter plate at a temperature greater than 900° C.

* * * * *